United States Patent [19]

Coates

[11] Patent Number: 4,704,107
[45] Date of Patent: Nov. 3, 1987

[54] ABSORBENT ARTICLE

[75] Inventor: John Coates, Toledo, Ohio

[73] Assignee: Colgate-Palmolive Company, New York, N.Y.

[21] Appl. No.: 407,004

[22] Filed: Aug. 10, 1982

Related U.S. Application Data

[63] Continuation of Ser. No. 224,722, Jan. 13, 1981, abandoned, which is a continuation of Ser. No. 75,484, Sep. 20, 1979, abandoned, which is a continuation-in-part of Ser. No. 946,933, Sep. 28, 1978.

[51] Int. Cl.$^4$ ............................................. A61B 19/00
[52] U.S. Cl. .................................... 604/357; 128/155; 128/156
[58] Field of Search ....................... 128/156, DIG. 30; 504/358, 378

[56]   References Cited
U.S. PATENT DOCUMENTS

| | | | |
|---|---|---|---|
| 3,416,525 | 12/1968 | Yeremian | 128/156 |
| 3,645,835 | 2/1972 | Hodgson | 128/132. D |
| 3,971,766 | 7/1976 | Ono et al. | 128/132. D |
| 3,975,570 | 8/1976 | Ono et al. | 128/156 |
| 3,999,547 | 12/1976 | Hernandez | 128/287 |
| 4,050,462 | 9/1977 | Woon et al. | 128/DIG. 30 |

Primary Examiner—Harvey E. Behrend
Assistant Examiner—T. J. Wallen
Attorney, Agent, or Firm—N. Blumenkopf; H. S. Sylvester; M. M. Grill

[57]   ABSTRACT

An absorbent article comprising, a liquid pervious top sheet, a backing sheet of fluid pervious material, an absorbent pad intermediate the top and backing sheets, and a coating of breathable adhesive substantially covering a front surface of the backing sheet facing the pad to define a liquid repellent barrier for liquids received in the pad. The backing sheet also has a pair of opposed end sections extending past end edges of the top sheet and having a coating of adhesive on the front surface, and a pair of release sheets covering the adhesive on the end sections. The article is useful as a surgical dressing, as a disposable diaper, sanitary napkin or the like products, particularly for absorbing aqueous body fluids.

3 Claims, 5 Drawing Figures

U.S. Patent   Nov. 3, 1987   4,704,107
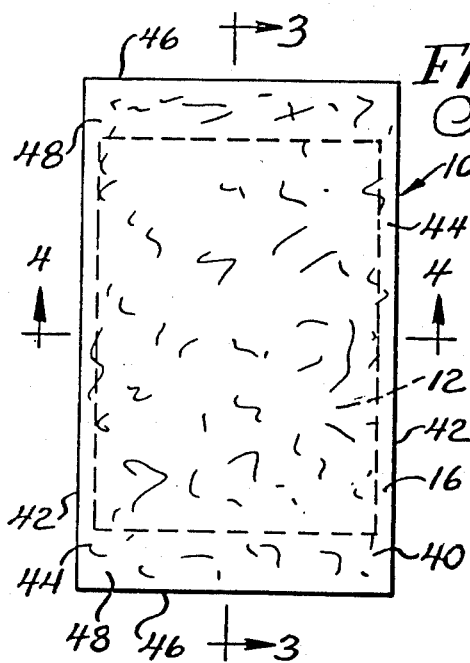
Fig. 1
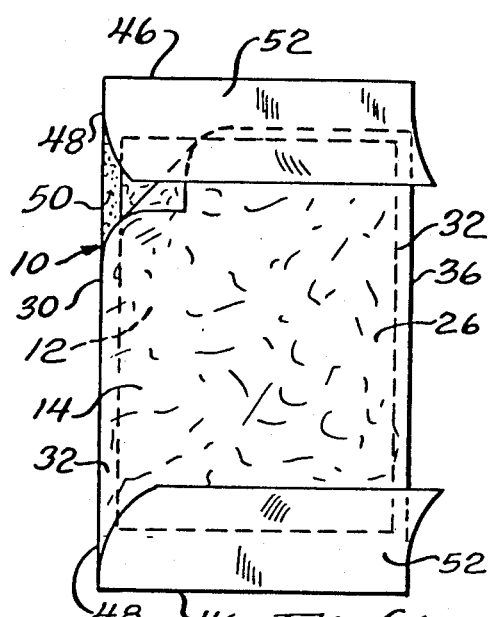
Fig. 2
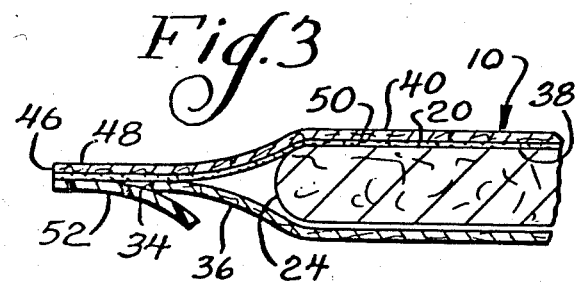
Fig. 3
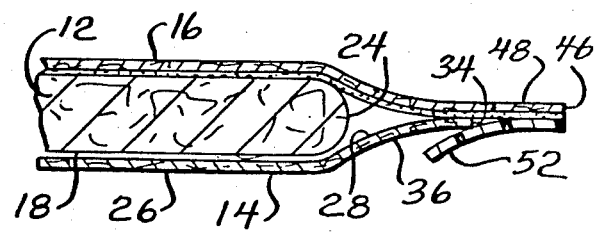
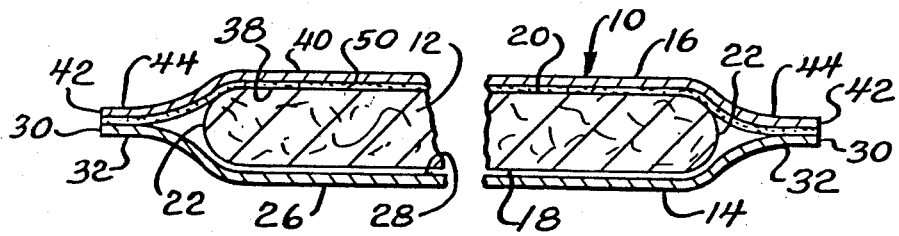
Fig. 4
Fig. 5
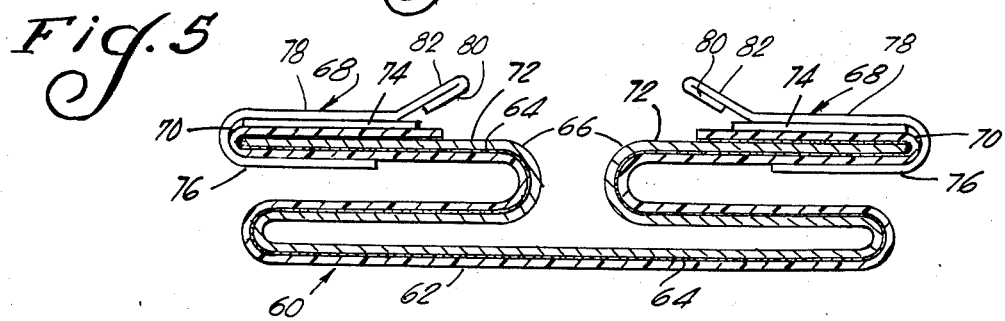

ABSORBENT ARTICLE

This is a continuation of application Ser. No. 224,722, abandoned filed 1-13-81 which is cont. of Ser. No. 75,484 filed 9-20-79, abandoned which is a continuation-in-part of my application Ser. No. 946,933 filed Sept. 28, 1978 entitled "Surgical Dressing".

BACKGROUND OF THE INVENTION

The present invention relates to absorbent articles, and more particularly to surgical dressings, disposable diapers, and sanitary napkins.

The typical manner of dressing a wound subsequent to surgery, such as in the abdominal region, is described as follows. First, a primary dressing, such as a guaze sponge is placed by the attendant over the wound. Next, an absorbent dressing, termed a secondary dressing, is placed over the primary dressing, and is secured in place. In use, body fluids pass through the primary dressing into the secondary dressing for absorption and retention therein.

Although such a dressing procedure has been utilized for many years, the prior secondary dressings do not provide an adequate barrier against passage of liquid completely through the secondary dressing, particularly if pressure is applied to the secondary dressing during use. Once liquid passes completely through the secondary dressing, termed "liquid strike through", the liquid provides a ready path for passage of bacteria through the dressing to the wound with possible deleterious results to the patient. However, it is not sufficient to merely place a liquid impervious barrier over the dressing to prevent "strike through", since the dressing must have the capability of passing water vapor and gas through the dressing to permit the wound to breathe and promote healing, and since usual liquid impervious barriers would prevent such breathing. Also, the prior dressings have required an excessive amount of time for the placement procedure, resulting in inconvenience to the hospital personnel.

Other absorbent articles such as disposable diapers and sanitary napkins are conventionally provided with liquid (usually water)—impervious backsheets and it is desirable that these articles also have "breathability" for improved comfort.

SUMMARY OF THE INVENTION

A principal feature of the present invention is the provision of an improved absorbent article of simplified construction.

The articles of the present invention comprise, a liquid pervious top sheet, a backing sheet of fluid pervious material, an absorbent pad intermediate the top and backing sheets, and a coating of adhesive substantially covering a front surface of the backing sheet facing the pad. The backing sheet has a pair of opposed end sections extending past end edges of the top sheet, and a pressure-sensitive adhesive on a front surface of the end sections. The absorbent device also has a pair of release sheets releasably attached to the adhesive on the end sections.

A feature of the present invention is that the adhesive on the backing sheet facing the pad provides a liquid repellent barrier, and minimizes the possibility of "liquid strike through" of body fluids during the use of the absorbent device.

Another feature of the invention is that the coated backing sheet is substantially impervious to passage of bacteria therethrough.

Thus, a feature of the present invention is that a dressing in accordance with this invention minimizes the possibility of contamination by bacteria to the patient's wound.

Another feature of the invention is that the adhesive is breathable to permit passage of air therethrough and in the case of a surgical dressing, promote healing of the patient's wound.

A further feature of the invention is that the adhesive contacts and stabilizes the pad when wetted during use.

Still another feature of the invention is that release sheets may be removed from end sections of the backing sheet to permit convenient attachment of the dressing to the patient through use of the end sections.

A feature of the present invention is that absorbent articles and in particular surgical dressings may be constructed in a simplified and inexpensive manner.

Further features will become more fully apparent in the following description of the embodiments of this invention and from the appended claims.

DESCRIPTION OF THE DRAWINGS

In the drawings:

FIG. 1 is a back plan view of a surgical dressing of the present invention;

FIG. 2 is a front plan view of the dressing of FIG. 1;

FIG. 3 is a fragmentary sectional view taken substantially as indicated along the line 3—3 of FIG. 1; and FIG. 4 is a fragmentary sectional view taken substantially as indicated along the line 4—4 of FIG. 1.

FIG. 5 is a sectional view at one end of a disposable diaper of the present invention.

DESCRIPTION OF THE PREFERRED EMBODIMENTS

Referring now to FIGS. 1-3, there is shown a surgical dressing generally designated 10 having an absorbent pad 12, a liquid pervious top sheet 14, and a backing sheet 16 of liquid pervious material. The pad 12 has a front surface 18, a back surface 20, a pair of side edges 22, and a pair of end edges 24 connecting the side edges 22. The pad 12 may be constructed from any suitable material, such as a mass of loosely formed cellulosic fibers formed by comminuting wood pulp, termed in the art of wood fluff.

The front or top sheet 14 has a front surface 26 for facing the patient during use of the dressing, and a back surface 28 facing the pad 12. The top sheet 14 also has a pair of opposed side edges 30 defining side margins 32 extending past the side edges of the pad 12, and a pair of opposed end edges 34 connecting the side edges 30 and defining a pair of opposed end margins 36 extending past the end edges 34 of the pad 12. The top sheet 14 may be made of a polyester-rayon nonwoven material, such as micrexed Novonette ® SP 117, a trademark of The Kendall Company, Boston, Mass.

The backing sheet 16 has a front surface 38 facing toward the pad 12, and a back surface 40 facing away from the patient during use of the dressing. The backing sheet 16 has a pair of opposed side edges 42 defining a pair of opposed side margins 44 extending past the side edges 22 of the pad 12, and a pair of end edges 46 connecting the side edges 32 and defining a pair of opposed end sections 48 extending past both the end edges 24 of the pad and the end edges 34 of the top sheet 14, with the end section 48 extending substantially the width of the dressing. In a suitable form, the backing sheet 16 may be constructed of the non woven material previously identified in connection with the top sheet 14.

The backing sheet 16 also has a layer or coating of liquid repellent, breathable adhesive 50 substantially covering the front surface 38 of the backing sheet 16 including the front surface of the backing sheet end sections 48. A suitable adhesive of this type comprises an acrylic based adhesive on a tape, product No. 1596, sold under the trademark Tenderskin by The Kendall Company, Boston, Mass. Thus, the adhesive 50 forms a liquid repellent barrier over the back surface 20 of the pad 12 in order to minimize the possibility of "liquid strike through" of body fluids during the use of the dressing, and provides a barrier against passage of bacteria to minimize the possibility of contamination to the patient's wound during the use of the dressing. The adhesive and backing sheet 16 permit passage of air therethrough, such that the dressing breathes to promote healing of the patient's wound. Further, the adhesive 50 may be utilized to bond the side margins 32 of the top sheet 14 to the side margins 44 of the backing sheet 16, in addition to the end margins 36 of the top sheet 14 to the inner portions of the backing sheet end sections 48. The adhesive 50 also contacts the back surface 20 of the pad 12 in order to stabilize the pad when wetted during use of the dressing. As shown, the dressing has a pair of release sheets 52 of suitable type releasably attached to and covering the adhesive 50 on the backing sheet end sections 48. Thus, the release sheets 52 may be peeled from the end sections 48 of the backing sheet 16 to expose the underlying adhesive 50 and permit convenient securement of the dressing to the patient by the end sections 48 during placement of the dressing.

Thus, in accordance with the present invention, the backing sheet 16 of the dressing has a suitable adhesive which provides a liquid repellent barrier for the dressing, and stabilizes the dressing pad during use. The adhesive on the backing sheet also may be utilized to secure the top and backing sheets together, and the backing sheet end sections and associated adhesive provide a convenient medium for attaching the dressing to the patient during placement, thus eliminating the need for separate tape strips or securing devices. It will also be apparent that the dressing of the present invention may be constructed in a simplified manner and at a reduced cost by merely spreading adhesive on the backing sheet and securing the components of the dressing together.

The present invention, as pointed out above, is also applicable to many other diverse structures as conventionally found in the disposable diaper and sanitary napkin field wherein there are present at least the basic elements of a pervious top sheet, a backing sheet and an absorbent means between said other two elements. Generally, in these structures, the backing sheet has been a liquid impervious member such as a film of polyethylene. In all of these structures the present invention is applicable by substituting the breathable, liquid repellent adhesive-coated fluid pervious backsheet shown herein for the liquid impervious backsheets heretofore used. Examples of suitable structures can be found in U.S. Pat. Nos. 4,047,531; 4,050,462; 4,054,141; 4,055,180; 4,055,184; 5,057,016; 4,072,151; 4,090,515; 4,090,516; 4,100,922; and 4,108,179.

The foregoing detailed description is given for clearness of understanding only, and no unnecessary limitations should be understood therefrom, as modifications will be obvious to those skilled in the art.

With particular reference to FIG. 5, 60 represents the diaper having a fluid pervious back sheet 62, carrying a layer or coating of liquid repellent, breathable adhesive 64 similar to 50 in FIG. 3, a fluid pervious top sheet 66 and an absorbent pad therebetween (not shown). A suitable tape fastener 68 is shown adjacent side edges 70 attached to front surface 72 of the diaper. A tape release sheet 74 is also shown attached to the diaper front surface. The fastener 68 has one end 76 secured to the diaper back sheet and a securement portion 78 releasably attached to the release sheet 74. Tabs 80 at end 82 are provided for releasing the fastener for use.

What is claimed is:

1. An absorbent article having a crotch region and comprising a liquid pervious top sheet, a backing sheet of fluid pervious material, an absorbent pad intermediate said top sheet and said backing sheet, and a coating of breathable liquid repellent adhesive substantially covering a front surface of said backing sheet facing said pad to define a liquid repellent barrier for liquids received in said pad while permitting breathing of the article, the marginal edges of said backing and top sheets being secured together around the periphery of the pad by said adhesive, said top sheet including a pair of opposed end edges, said backing sheet having a pair of opposed end sections extending past the end edges of said top sheet, said end sections including said adhesive on said front surface, and a pair of release sheets releasably attached to said adhesive on said end sections, said opposed edges having elastic means in at least the crotch region of the absorbent article, said elastic means being attached by said adhesive to said backing sheet.

2. The article of claim 1, wherein said top sheet and said backing sheet comprise non-woven material.

3. The article of claim 1, wherein said adhesive comprises an acrylic based adhesive.

* * * * *